United States Patent [19]
Seay, Jr.

[11] Patent Number: 5,139,030
[45] Date of Patent: Aug. 18, 1992

[54] RETINA TESTER

[76] Inventor: James I. Seay, Jr., 3637 Park Ave., #311, Memphis, Tenn. 38111

[21] Appl. No.: 682,310

[22] Filed: Apr. 9, 1991

[51] Int. Cl.$^5$ .............................................. A61B 13/00
[52] U.S. Cl. ..................................................... 128/745
[58] Field of Search ............... 128/745; 351/224, 243, 351/246; 362/362, 364, 365, 367, 368

[56] References Cited

U.S. PATENT DOCUMENTS

| | | | |
|---|---|---|---|
| 3,288,546 | 11/1966 | Gans | 128/745 |
| 4,058,113 | 11/1977 | Fields | 128/745 |
| 4,146,311 | 3/1979 | Murr | 128/745 |
| 4,818,091 | 4/1989 | Sadum et al. | 351/224 |

FOREIGN PATENT DOCUMENTS 2507723  8/1976  Fed. Rep. of Germany ...... 128/745

Primary Examiner—Max Hindenburg
Attorney, Agent, or Firm—Walker, McKenzie & Walker

[57] ABSTRACT

A retina tester for testing a person's retina for macular degeneration. The retina tester includes a grid having a grid pattern and having an aperture through the center of the grid pattern; and includes illuminating structure for illuminating the aperture through the center of the grid pattern of the grid.

18 Claims, 2 Drawing Sheets 5,139,030

RETINA TESTER

BACKGROUND OF THE INVENTION

1. Field of the Invention

The present invention relates, in general, to an apparatus for use in testing the retina for macular degeneration or the like.

2. Information Disclosure Statement

The macula is the portion of the retina of a person's eye which allows that person to see detail. Macular degeneration will cause a person's vision in the affected eye to become distorted, blurred, discolored, or otherwise abnormal. An Amsler grid is used by many people to test the vision in each eye, separately, for macular degeneration. The Amsler grid consists in general of a grid composed of a plurality of spaced apart horizontal and vertical lines forming a plurality of squares of the same size, and having a dot in the very center thereof. Typical instructions for using the Amsler grid are as follows:

A. Wear reading glasses if you normally use reading glasses.
B. Cover one eye.
C. Look at the center dot and keep your vision on it at all times.
D. While looking directly at the center of the grid, and only at the center of the grid, be sure that all the lines are straight and all the squares are the same size.
E. If you notice any area on the grid that becomes distorted, blurred, discolored, or otherwise abnormal, please call you doctor right away.
F. Do this for each eye.

A modified version of the Amsler grid has been developed for use by patients especially after laser treatment for certain forms of macular degeneration. In this modified version, the center dot is replaced with a large "X" that extends from each corner of the grid and crosses at the very center thereof. The use of this modified Amsler grid is substantially the same as given above, except that the tester looks at the center portion of the "X" rather than at the center dot. It is important when using this modified Amsler grid that the tester keeps his or her vision on the center portion of the "X" at all times. However, since a patient after such laser treatment will always notice an area of abnormality on the Amsler grid, rather than making sure that all the lines are straight and all the squares are the same size, these patients, while looking directly at the center of the grid (i.e., at the center portion of the "X"), and only at the center of the grid, will make note of any change in the area of abnormality.

A problem many people with macula degeneration have with using an Amsler grid, especially those who have had laser treatment, is that sometimes the abnormality in that eye being tested is such that the center dot of the Amsler grid is distorted, blurred, or otherwise abnormal, making it difficult, if not impossible, for that person to look at the center dot and keep his or her vision on the center dot at all times during the test.

The prior art does not disclose or suggest the present invention. More specifically, nothing in the prior art, taken as a whole, discloses or suggests a retina tester including a grid having a grid pattern and having an aperture through the center of the grid pattern; and including illuminating means for illuminating the aperture through the center of the grid pattern of the grid.

SUMMARY OF THE INVENTION

The present invention is directed toward providing an improved device for allowing a person to test his or her retinas. The concept of the present invention is to provide an Amsler-like grid with a lighted center "dot" to allow people to accurately make an Amsler-type test of each eye even if that person has an abnormality which hinders that person from looking at the center dot and keeping his or her vision on the center dot at all times during the test.

The retina tester of the present invention is used to test a person's retina for macular degeneration and includes, in general, a grid having a grid pattern and having an aperture through the center of the grid pattern; and includes illuminating means for illuminating the aperture through the center of the grid pattern of the grid.

DESCRIPTION OF THE PREFERRED EMBODIMENT

Figure 1:
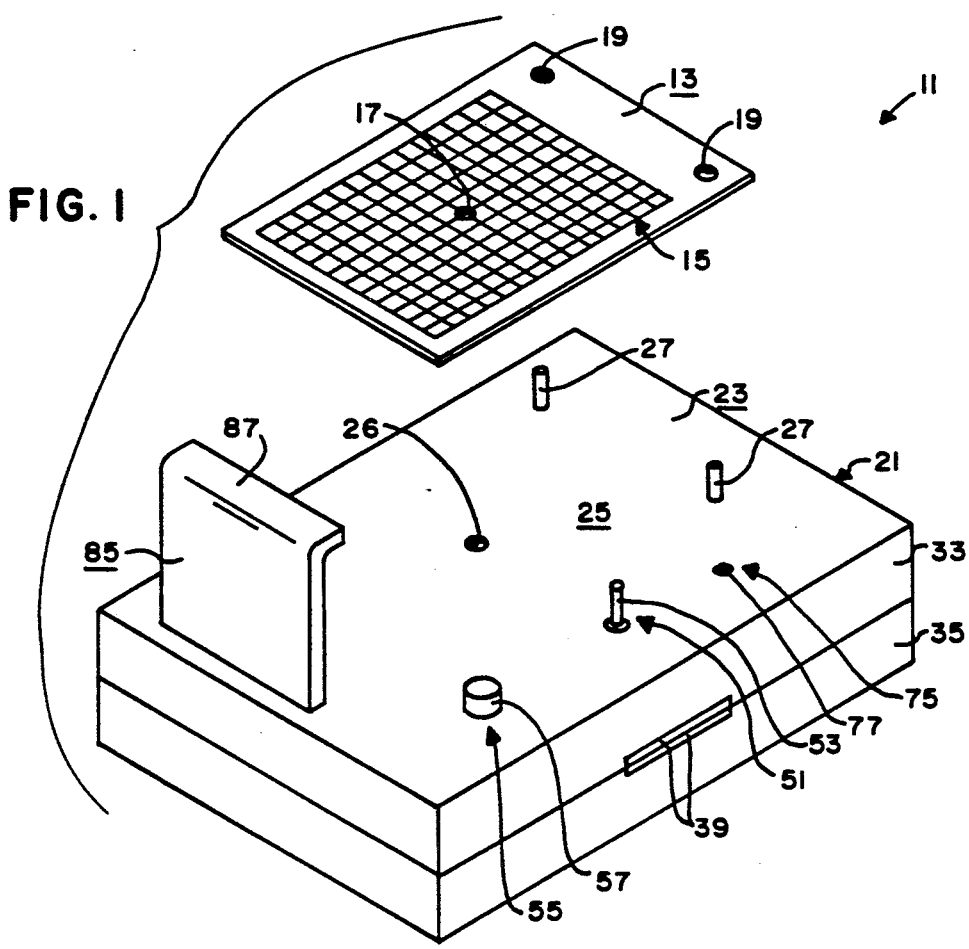
FIG. 1 is an exploded perspective view of the retina tester of the present invention.
Figure 2:
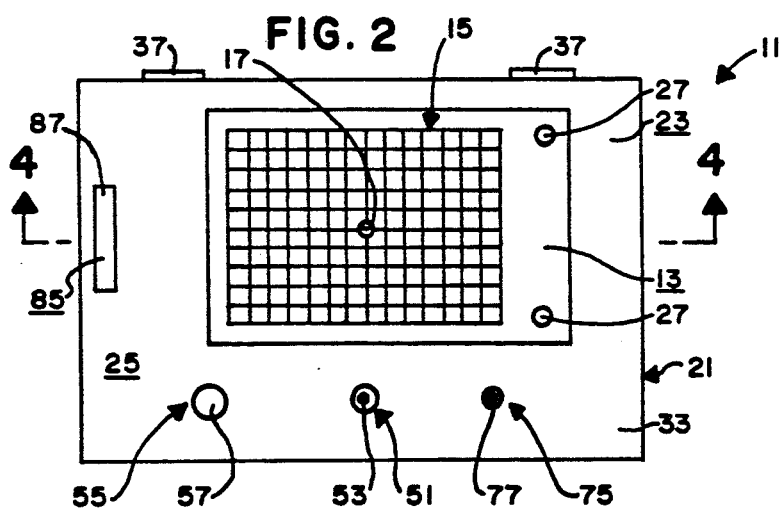
FIG. 2 is a top plan view thereof.
Figure 3:
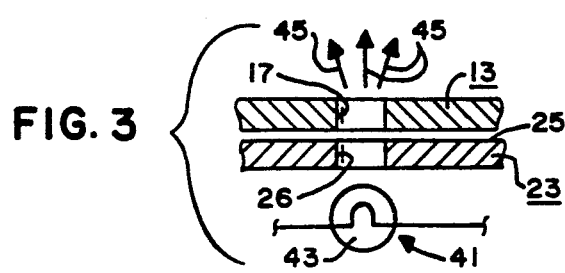
FIG. 3 is an enlarged, somewhat diagrammatic sectional view of a portion of the retina tester of the present invention.
Figure 4:
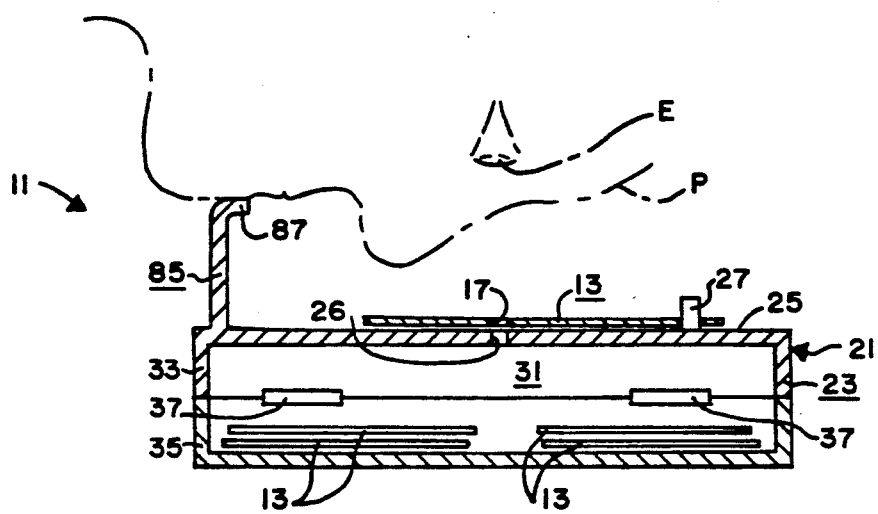
FIG. 4 is a sectional view substantially as taken on line 4—4 of FIG. 2 with portions of the retina tester omitted for clarity and with a portion of a tester's head shown in broken lines.

The preferred embodiment of the retina tester of the present invention is shown in FIGS. 1-5 and identified by the numeral 11. The retina tester 11 was invented when the inventor learned that he had macular degeneration and began the prescribed testing using an Amsler grid. Because of the inventor's visual limitations, he had problems seeing the center of the Amsler grid and, thus, found it difficult, if not impossible, to properly follow the prescribed testing procedures using the Amsler grid. The retina tester 11 illuminates the center of an Amsler-type grid to make it easy for a person P testing his or her vision for macular degeneration or the like, to look at the center of the grid and keep his or her vision on the center of the grid at all times during a test.

The retina tester 11 includes a grid 13 having a grid pattern 15 preferably formed by a network of uniformly spaced first lines and a plurality of uniformly spaced second lines. Except for the center first line and the center second line, all the first lines cross all the second lines at 90 degree angles to define a plurality of regular boxes or squares. The center first line and the center second line are arranged so that they would cross one another at the exact center of the grid pattern 15. However, the grid 13 has an aperture 17 at the exact center of the grid pattern 15 to thus prevent the center first line and the center second line from crossing one another. The grid 13 is preferably formed out of a piece of paper with the grid pattern 15 printed thereon and with the aperture 17 punched or otherwise formed in the exact center of the grid pattern 15. A spaced apart pair of positioning apertures 19 are preferably punched or otherwise formed in the grid 13 at a location above the grid pattern 15 as clearly shown in FIG. 1 and for reasons which will hereinafter become apparent. Various spaces, blank lines, indicia or the like may be provided on the grid 13 to allow the person P to write certain information on the grid 13 concerning a certain test, etc.

The retina tester 11 includes illumination means 21 for illuminating the aperture 17 and for helping a person P testing his or her vision for macular degeneration or the like, to look at the center of the grid pattern 15 and keep his or her vision on the center of the grid pattern 15 at all times during a test even if that person P has visual limitations which cause problems seeing the center of the grid pattern 15.

The illumination means 21 preferably includes a body 23 having a support surface 25 for supporting the grid 13. The support surface 25 preferably has an aperture 26 therein for being aligned with the aperture 17 of the grid 13 supported on the support surface 25 for reasons which will hereinafter become apparent. The support surface 25 preferably includes a pair of spaced apart peg members 27 for extending through the apertures 19 of the grid 13 when the grid 13 is supported by the support surface 25 to properly position and hold the grid 13 on the body 23 with the aperture 17 thereof aligned with the aperture 26 through the support surface 25, etc., as will now be apparent to those skilled in the art. The body 23 preferably includes a box member having a hollow interior 31 for containing certain components of the illumination means 21 and for containing used and unused grids 13. More specifically, the box member preferably includes a first half 33 and a second half 35 joined together by hinge means 37 which allows the box member to be opened so that access to the used and unused grids 13 is provided, etc., as will now be apparent to those skilled in the art. Closure means 39 is preferably provided for holding the first and second halves 33, 35 closed. The closure means 39 may consist merely of coacting Velcro ® members or the like fixedly attached to the first and second halves 33, 35 on the sides thereof opposite the hinge mean 37 to thereby securely hold the first and second halves 33, 35 in a closed position and require deliberate force to be used to open the box member as will now be apparent to those skilled in the art.

The illumination means 21 includes light means 41 for directing light to the aperture 26 in the support surface 25 and the aperture 17 of the grid 13 positioned on the support surface 25 of the body 23. The light means 41 preferably includes an electric light bulb 43 for being securely mounted in the interior 31 of the box member in a position to direct light to the aperture 26 in the support surface 25 and the aperture 17 of the grid 13 positioned on the support surface 25 of the body 23 as indicated by the arrows 45 in FIG. 3.

Figure 5:
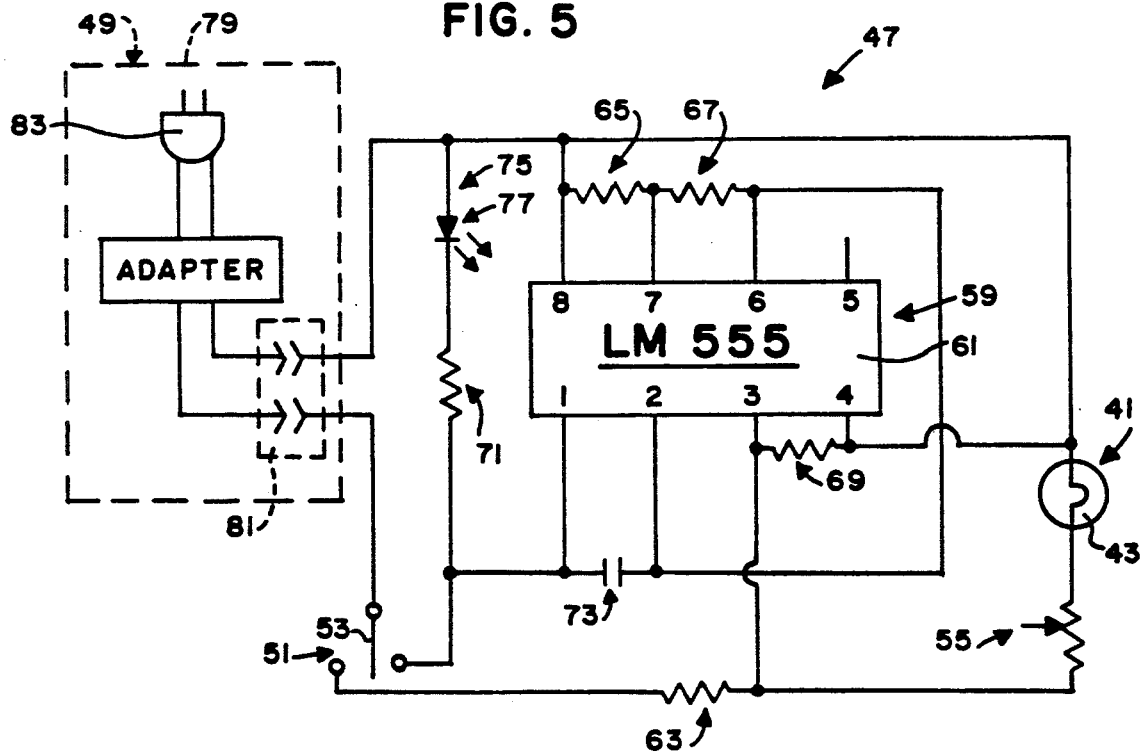
FIG. 5 is a schematic view of the electrical circuitry of the retina tester of the present invention.

The illumination means 21 includes a source 49 of electrical energy and a circuit 47 for coupling the light means 41 to the source 49 of electrical energy as shown in FIG. 5.

The circuit 47 preferably includes a switch 51 for allowing the person P to selectively activate and deactivate the light means 41. The switch 51 preferably has a control member such as a control lever 53 physically positioned on the support surface 25 of the body 23 in such a position that the switch 51 can be easily controlled by the person P during a test, as will now be apparent to those skilled in the art. The switch 51 is preferably a standard double pole, double throw, center-off toggle switch or the like of any well known construction to allow the person P to move the control lever 53 in one direction from the center-off position to a constant light position for causing the light means 41 to emit a constant, steady light, or to move the control lever 53 in the other direction from the center-off position to a blinking light position for causing the light means 41 to emit a blinking or pulsing light as will hereinafter become apparent.

The circuit 47 preferably includes a first resistor for controlling the intensity of the light emitted from the light means 41. The first resistor preferably includes an adjustable resistor 55, such as a rheostat or potentiometer, for allowing the person P to adjust the intensity of the light emitted from the light means 41 The adjustable resistor 55 is preferably a standard 2 watt, 50 ohm potentiometer. The adjustable resistor 55 preferably has a control knob 57 located above the support surface 25 of the body 23 in such a position that the adjustable resistor 55 can be easily controlled by the person P during a test, etc., as will now be apparent to those skilled in the art.

The circuit 47 preferably includes timing means 59 for causing the light means 41 to emit a blinking or pulsing light and for controlling the duration of the pulse or blink when the switch 51 is in the blinking light position. The timing means 59 preferably includes a standard 555 integrated circuit 61 such as a National Semiconductor Corporation LM 555 timer, or the equivalent. The circuit 47 preferably includes a second resistor 63 (e.g., a standard 1 watt, 0.15 ohm resistor), a third resistor 65 (e.g., a standard 5.6 kilohm resistor), a fourth resistor 67 (e.g., a standard 1 megohm resistor), a fifth resistor 69 (e.g., a standard 5.6 kilohm resistor), a sixth resistor 71 (e.g. a standard 220 ohm resistor), and a capacitor 73 (e.g., a standard 0.01 microfarad capacitor) electrically coupled to one another, to the light means 41, to the source 49 of electrical energy, to the switch 51, to the adjustable resistor 55, and to the LM 555 integrated circuit 61 as shown schematically in FIG. 5 and as will now be apparent to those skilled in the art.

An indicator light 75 is preferably mounted in the circuit 47 as shown schematically in FIG. 5 for indicating when the circuit 47 is electrically activated (i.e., for indicating when the circuit 47 is coupled to the source 49 of electrical energy and the control lever 53 of the switch 51 is positioned in either the constant light position or the blinking light position. The indicator light 75 preferably includes a standard red light emitting diode 77 physically positioned relative to the support surface 25 of the body 23 in such a position that the light emitted thereby can be easily seen by the person P during a test, etc., as will now be apparent to those skilled in the art.

The source 49 of electrical energy may consist simply of a 12 volt battery. Preferably, the source 49 of electrical energy includes a standard AC-to-DC adapter 79 having first plug means 81 for being electrically coupled to the circuit 47 as indicated schematically in FIG. 5 to provide 12 volt direct current to the circuit 47, and having a second plug means 83 for being electrically coupled to a standard 120 volt alternating current outlet as will now be apparent to those skilled in the art. The adapter 79 will thus convert 120 volt alternating current to 12 volt direct current as will now be apparent to those skilled in the art.

The retina tester 11 preferably includes positioning means 85 for helping the person P maintain the same distance from the grid pattern 15 throughout a test and during subsequent tests. The positioning means 85 preferably includes a chin support 87 attached to and extending upwardly from the support surface 25 of the body 23 at a location to engage the chin of the person P when the person P is properly positioned for a test relative to the support surface 25. The chin support 87 may be constructed from a rigid length of plastic or the like with one end thereof fixedly attached to the support surface 25.

The operation and use of the retina tester 11 is quite simple. First, a grid 13 is positioned on the support surface 25 with the peg members 27 extending through the respective apertures 19 and with the aperture 17 aligned with the aperture 26. Next, with the source 49 of electrical energy coupled to the circuit 47, the control lever 53 is moved to the constant light position. The light means 41 will then illuminate the aperture 17. The intensity of the light emitted by the light bulb 43 can be varied, if desired, by the adjustable resister 55. The retina tester 11 should be used on a table or the like in normal light. The person P should wear reading glasses if he or she normally wears such glasses when reading. The eye E to be tested is positioned about 76.2 millimeters (3 inches) over the aperture 17 through the grid pattern 15. The chin support 87 may be used to keep the eye E at the same distance from the aperture 17. The person P should *stare steadily* at the illuminated aperture 17 and draw the outline of any obstruction noted directly onto the grid pattern 15. If the person P has difficulties outlining the obstruction, vertical and horizontal lines should be drawn to outline the limits of the obstruction at the top, bottom, and both sides of the obstruction. If the person P experiences difficulties in concentrating on the center of the grid pattern 15, the control lever 53 should be moved to the blinking light position. Likewise, varying the intensity of the light emitted by the light bulb 43 by rotating the control knob 57 of the adjustable resistor 55 might help penetrate any clot or the like making it difficult for the person P to look at the illuminated aperture 17. A single grid 13 should be used daily for an entire week with a different color pen or pencil used each day to draw the obstruction. The date of each test and the color of the pen or pencil used to draw the outline for each test should be noted on the grid 13. The used grid 13 should be kept for examination by the person's physician. After the test, the control lever 53 should be moved back to the center off position.

It should be noted that the retina tester 11 does not cure the eye. It only allows one to observe any changes which may be noted in an eye on account of macular degeneration. The retina tester 11 is intended to be used daily on both eyes and the person's physician should be notified immediately if any change is observed.

Although the present invention has been described and illustrated with respect to a preferred embodiment and a preferred use therefor, it is not to be so limited since modifications and changes can be made therein which are within the full intended scope of the invention.

I claim:

1. A retina tester for testing a person's retina for macular degeneration; said retina tester comprising:

a) a grid having a grid pattern and having an aperture through the center of said grid pattern; and b) illuminating means for illuminating said aperture through said center of said grid pattern of said grid; said illuminating means including a body having a support surface for supporting said grid; said support surface of said body having means for being aligned with said aperture through the center of said grid pattern of said grid.

2. The retina tester of claim 1 in which said grid pattern includes a network of uniformly spaced first lines and a plurality of uniformly spaced second lines crossing said first lines, and in which all the first lines of said grid pattern cross all the second lines of said grid pattern at 90 degree angles except for the center one of said first lines and the center one of said second lines.

3. A retina tester for testing a person's retina for macular degeneration; said retina tester comprising:

a) a grid having a grid pattern and having an aperture through the center of said grid pattern; and b) illuminating means for illuminating said aperture through said center of said grid pattern of said grid; said illuminating means including a body having a support surface for supporting said grid, said support surface of said body having an aperture therein for being aligned with said aperture through said center of said grid pattern of said grid.

4. The retina tester of claim 3 in which said grid has a pair of spaced apart positioning apertures therethrough, and in which said support surface of said body of said illuminating means includes a pair of spaced apart peg members for extending through said positioning apertures through said grid to properly position and hold said grid on said body with said aperture through said center of said grid pattern aligned with said aperture in said support surface of said illumination means.

5. The retina tester of claim 4 in which is included a plurality of used and unused grids; and in which said body of said illumination means includes a box member having a hollow interior for containing said used and unused grids.

6. The retina tester of claim 5 in which said box member includes a first half, a second half, and hinge means for joining said first and second halves together and for allowing said box member to be opened to allow access to said hollow interior thereof.

7. The retina tester of claim 6 in which said box member includes closure means for holding said box member closed.

8. The retina tester of claim 3 in which said illumination means includes light means for directing light to said aperture in said support surface of said body and to said aperture in said center of said grid pattern of said grid positioned on said support surface of said body.

9. The retina tester of claim 8 in which said light means includes an electric light bulb; and in which said illumination means includes a source of electrical energy and a circuit for coupling said light means to said source of electrical energy.

10. The retina tester of claim 9 in which said circuit includes a switch for allowing said light means to be selectively activated and deactivated, said switch having a control member positioned on said support surface of said body for allowing said light means to be selectively activated and deactivated during a test by a person being tested.

11. The retina tester of claim 10 in which said circuit includes an adjustable resistor for controlling the intensity of the light emitted from said light means.

12. The retina tester of claim 11 in which said circuit includes timing means for causing said light means to emit a blinking light.

13. The retina tester of claim 10 in which said circuit includes an indicator light for indicating when said circuit is electrically activated.

14. The retina tester of claim 3 in which is included positioning means for helping the person being tested maintain a certain distance from said grid pattern throughout a test.

15. The retina tester of claim 14 in which said position means includes a chin support attached to and extending upward from said support surface of said body of said illumination means at a position for engaging the chin of the person being tested.

16. A retina tester for testing a person's retina for macular degeneration; said retina tester comprising:
   a) a grid having a grid pattern formed by a network of uniformly spaced first lines and a plurality of uniformly spaced second lines crossing said first lines, and having an aperture through the center of said grid pattern; all the first lines of said grid pattern crossing all the second lines of said grid pattern at 90 degree angles except for the center one of said first lines and the center one of said second lines; said grid having a pair of spaced apart positioning apertures therethrough;
   b) illuminating means for illuminating said aperture through said center of said grid pattern of said grid; said illumination means including a body having a support surface for supporting said grid; said support surface of said body having an aperture therein for being aligned with said aperture through said center of said grid pattern of said grid; said support surface including a pair of spaced apart peg members for extending through said positioning apertures through said grid to properly position and hold said grid on said body with said aperture through said center of said grid pattern aligned with said aperture in said support surface of said illumination means; said illumination means including light means for directing light to said aperture in said support surface of said body and to said aperture in said center of said grid pattern of said grid positioned on said support surface of said body; said illumination means including a source of electrical energy and a circuit for coupling said light means to said source of electrical energy; said circuit including an adjustable resistor for controlling the intensity of the light emitted from said light means; and
   c) positioning means for helping the person being tested maintain a certain distance from said grid pattern throughout a test.

17. Illuminating means for use with a grid having a grid pattern thereon for testing a person's retina for macular degeneration; said illuminating means comprising:
   a) a body having a support surface for supporting said grid; said support surface of said body having an aperture therein for being aligned with the center of said grid pattern of said grid; said support surface including means for properly positioning and holding said grid on said body with the center of said grid pattern aligned with said aperture in said support surface of said illumination means;
   b) light means for directing light to said aperture in said support surface of said body and to the center of said grid pattern of said grid positioned on said support surface of said body;
   c) a source of electrical energy; and
   d) a circuit for coupling said light means to said source of electrical energy.

18. Illuminating means for use with a grid having a grid pattern thereon for testing a person's retina for macular degeneration; said illuminating means comprising;
   a) a body having a support surface for supporting said grid; said support surface of said body having means for being aligned with the center of said grid pattern of said grid; said support surface including means for properly positioning and holding said grid on said body with the center of said grid pattern aligned with said means for being aligned with the center of said grid pattern of said grid;
   b) light means for illuminating said means for being aligned with the center of said grid pattern of said grid and the center of said grid pattern of said grid positioned on said support surface of said body;
   c) a source of electrical energy; and
   d) a circuit for coupling said light means to said source of electrical energy.

* * * * *